(12) United States Patent
Kennedy et al.

(10) Patent No.: US 6,488,952 B1
(45) Date of Patent: Dec. 3, 2002

(54) SEMISOLID THERAPEUTIC DELIVERY SYSTEM AND COMBINATION SEMISOLID, MULTIPARTICULATE, THERAPEUTIC DELIVERY SYSTEM

(76) Inventors: John P. Kennedy, 213 Honeysuckle La., Winchester, KY (US) 40391; Curtis E. Jones, II, 2 A Town Park La., Charleston, SC (US) 29412

( * ) Notice: Subject to any disclaimer, the term of this patent is extended or adjusted under 35 U.S.C. 154(b) by 0 days.

(21) Appl. No.: 09/941,378

(22) Filed: Aug. 28, 2001

(51) Int. Cl.$^7$ .............................. A61F 2/02; A61K 9/50
(52) U.S. Cl. ..................... 424/426; 424/501; 424/502
(58) Field of Search ..................... 424/426, 501, 424/502

(56) References Cited

U.S. PATENT DOCUMENTS

| | | | | |
|---|---|---|---|---|
| 5,320,840 A | * | 6/1994 | Camble et al. | 424/85.1 |
| 5,360,610 A | * | 11/1994 | Tice et al. | 424/426 |
| 6,028,164 A | | 2/2000 | Loomis | |
| 6,051,576 A | | 4/2000 | Ashton et al. | |
| 6,096,338 A | | 8/2000 | Lacy et al. | |
| 6,102,887 A | | 8/2000 | Altman | |
| 6,120,789 A | | 9/2000 | Dunn | |
| 6,153,212 A | | 11/2000 | Mao et al. | |
| 6,277,413 B1 | * | 8/2001 | Sankaram | 424/501 |
| 6,248,363 B1 | * | 9/2001 | Patel et al. | 424/497 |

* cited by examiner

Primary Examiner—Carlos Azpuru
(74) Attorney, Agent, or Firm—P. Jeff Martin (57) ABSTRACT

A semisolid therapeutic delivery system and combination semisolid, multiparticulate therapeutic delivery system for therapeutic applications is provided which includes a biocompatible semisolid delivery system and a biocompatible combination semisolid, multiparticulate delivery system for injection, deposition, or implantation within the body to facilitate local or systemic therapeutic effects through the actions of incorporated medicaments or actions inherit to the system.

55 Claims, 3 Drawing Sheets

SEMISOLID THERAPEUTIC DELIVERY SYSTEM AND COMBINATION SEMISOLID, MULTIPARTICULATE, THERAPEUTIC DELIVERY SYSTEM

RELATED APPLICATIONS

There are no previously filed, or currently any co-pending applications, anywhere in the world.

BACKGROUND OF THE INVENTION

1. Field of the Invention

The present invention relates generally to biocompatible materials for systemic and local delivery of therapeutic agents directly within or upon body tissues and, more particularly, to a semisolid therapeutic delivery system and combination semisolid, multiparticulate therapeutic delivery system for therapeutic agents.

2. Description of the Related Art

Approximately 35,000 new brain tumors are diagnosed in adults annually in the U.S. Central nervous system (CNS) malignancies, specifically malignant gliomas, account for 2.5% of all cancer related deaths. Malignant gliomas are the third leading cause of cancer related deaths of persons between the ages of 15 and 34.

In view of the fact that CNS malignancy research has been limited in comparison to other areas of cancer research, this particular malignancy will almost assuredly rise as one of the leading causes of cancer deaths in the U.S.

Malignant gliomas result in tumor formation within the central nervous system. These tumors rapidly grow and infiltrate normal tissues, which result in enlarged tumors compressing normal brain tissue, and in turn, cause abnormality and usually necrosis within the tumor itself, thus requiring removal of the tumor.

Conventional methods of cancer treatment include surgical removal, radiation and chemotherapy. Surgical removal is the initial treatment of choice. Subsequent radiation therapy operates to effectuate physical damage to malignant cells so as to render them incapable of cell division. Chemotherapy generally involves administering drugs that alter the normal structure, function and replication of DNA. Chemotherapy has generally been of limited utility in malignant gliomas due to the fact that most chemotherapeutic agents have very poor penetration into the central nervous system. As a result, clinicians are forced to dose these agents in an aggressive manner in order to increase the systemic concentration to force the drug into the central nervous system. Such aggressive therapy often results in dose proportional systemic side effects such as depression and impairment of normal bone marrow function, which leaves the patient susceptible to a multitude of infections due to the depletion of normal white blood cells. In addition, these agents are toxic to many organ systems including the liver, kidneys, and lungs.

Consequently, conventional treatment methods with respect to malignant gliomas have resulted in a very dismal long-term prognosis, with a mean 24-month survival of 15-20% of patients. Thus, approximately 85% of patients suffering from a malignant glioma will die within the first two years following diagnosis. This stems from an unusually high rate of tumor recurrence due to incomplete surgical resection. Malignant cells usually infiltrate normal tissue surrounding the primary focus itself and are left behind; hence the need for radiation and chemotherapy following surgical removal of the tumor.

In order to remedy inefficient delivery of chemotherapeutic agents so as to prevent reoccurrence of malignant tumors, pharmaceutical scientists developed the concept of local drug delivery. This concept involves the instillation or application of a drug directly to a sight of action; i.e., the brain. This theoretical strategy led to the development of a drug loaded wafer composed of a biodegradable, polyanhydride polymer, manufactured under the brand name Biodel® by Guilford Pharmaceuticals Inc., Baltimore, Md. The chemical name for the polymer system is poly[bis(p-carboxyphenoxy)propane: sebacic acid]. The drug-loaded wafers, Gliadel® Wafers, are of a solid, disc-shaped configuration approximately the size of a dime. Each wafer is approximately 1.4 centimeters in diameter, approximately 1 mm in thickness and weighs approximately 200 milligrams. Each wafer contains approximately 7.7 milligrams of a drug called BCNU, or carmustine. The chemical name for BCNU is 1,3-bis[2-chloroethyl]-1-nitrosourea. Historically, BCNU has been the common drug choice in the treatment of malignant gliomas primarily due to its ability to penetrate into the central nervous system from the systemic circulation in relatively high concentrations compared to other chemotherapeutic agents.

However, there are various problems associated with the implantation of Gliadel® Wafers. Firstly, due to the rigid nature of the wafer's configuration, the size and shape of the resection pocket may represent a significant problem and limitation of therapy. The clinically recommended dose of wafers to date has been from 6–8 wafers, which yields approximately between 46.2 and 61.6 milligrams BCNU. However, often in an attempt to retain as much viable brain tissue as possible, neurosurgeons find that the resection pocket contains insufficient void space to implant the entire course of therapy. In addition, in the very common case of an irregularly shaped tumor, the physical constraints may also compromise the therapeutic benefit. Further, in the case of a large tumor, the wafers, once secured in the resection pocket, may leave a considerable portion of the surface area without direct contact to the tissue.

Consequently, the rigid nature of the wafers seriously limits the ability of the system to directly contact all areas of tissue directly adjacent to the implants. The unexposed areas of tissue may contain tumor cells, thus leaving such cells untreated and viable. This results in areas receiving a preferential drug exposure while tissues which are removed from direct contact with the wafer(s) receive either suboptimal or, conceivably, no therapy.

In addition, after a neurosurgeon has removed the bulk of a tumor and has lined the resection pocket with Gliadel® Wafers, a large void volume remains. Neurosurgeons pack this void with bio-absorbent materials such as Gelfoam® (absorbable gelatin sponge) to secure the placement of the disks and to prevent brain tissue from herniating into the resection pocket. Thus the large void volume, which could be used for drug delivery, is inefficiently utilized.

There are also many practical problems associated with the handling of Gliadel® Wafers. The wafers are extremely fragile and often break into pieces when removed from their protective packaging. The manufacturer recommends that once a wafer has been broken into 3 or more pieces, it must be discarded.

In addition, the wafers must be maintained at a refrigerated temperature of 0° C. or colder for stability reasons. If the wafers are left at room temperature for 6 or more hours, they must be discarded.

Furthermore, with respect to economic factors, acquisition costs for 8 wafers is approximately $12,000 to $15,000.

Patient cost is significantly higher and given the current lack of strongly significant efficacy data, third party coverage is limited. Thus patient treatment is often prohibitively expensive.

Accordingly, there is a need for a semisolid delivery system and combination semisolid, multiparticulate delivery system for delivery of therapeutic agents systemically and locally to tissues after implantation, deposition or injection. This system efficiently utilizes the entire cavity, excavation, or void volume to increase drug dosages, optimizes the uniform delivery and consistent distribution of therapeutic agents to large, small and irregularly shaped compartments and to allow easy injection, placement or surgical implantation. The development of the multiparticulate and semisolid delivery system fulfills this need.

A search of the prior art did not disclose any patents that read directly on the claims of the instant invention; however, the following references were considered related.

U.S. Pat. No. 6,028,164 issued in the name of Loomis describes cross-linked compositions formed from a water insoluble copolymer having a bio-resorbable region wherein such compositions when placed in contact with an aqueous environment form hydrogels, which are useful as sealants for porous materials and particularly for implantable prostheses.

U.S. Pat. No. 6,051,576 issued in the name of Ashton et al. describes a means for improving pharmaceutical and pharmacological properties of pharmacologically active compounds or prodrugs by conjugating them together to form a co-drug.

U.S. Pat. No. 6,096,338 issued in the name of Lacy et al. describes a delivery system for hydrophobic drugs.

U.S. Pat. No. 6,102,887 issued in the name of Altman describes a catheter system for injecting therapeutic agents including large molecules into the body and a method for using the same.

U.S. Pat. No. 6,120,789 issued in the name of Dunn describes a method and composition for forming an implant in-situ within a body using non-polymeric materials, and the use of such implants as medical devices and drug delivery systems.

U.S. Pat. No. 6,153,212 issued in the name of Mao et al. describes biodegradable terephthalate polyester-poly (phosphonate) compositions, articles, and methods of using the same.

U.S. Pat. No. 6,228,393 issued in the name of DiCosmo et al. describes drug delivery via therapeutic hydrogels.

U.S. Pat. No. 6,201,072 issued in the name of Rathi et al. describes biodegradable low molecular weight triblock poly (lactide-co-glycolide)polyethylene glycol copolymers having reverse thermal gelation properties.

U.S. Pat. No. 6,201,065 issued in the name of Pathak et al. describes multiblock biodegradable hydrogels for drug delivery and tissue treatment.

U.S. patent application Ser. No. 20010000728 submitted in the name of Sawhney et al. describes compliant tissue sealants.

U.S. patent application Ser. No. 20010000142 submitted in the name of Santos et al. describes methods and compositions for enhancing the bioadhesive properties of polymers using organic excipients.

Consequently, a need has been demonstrated for providing an implantable, depositable and/or injectable biocompatible delivery system for sustained and/or immediate local and/or systemic delivery of drugs and therapeutic agents by the invention.

SUMMARY OF THE INVENTION

Therefore, it is an object of the present invention to provide an implantable, depositable, and/or injectable delivery system for immediate, sustained local or systemic delivery of drugs and therapeutic agents.

It is another object of the present invention to provide a biodegradable, biocompatible delivery system for drugs and therapeutic agents.

It is another object of the present invention to provide a delivery system, which can provide for the solubilization, stabilization of lipophilic drug compounds in concentrations necessary for therapeutic benefit over the course of therapy.

It is another object of the present invention to provide a delivery system which is malleable and thus can be delivered and manipulated within an implant site so as to conform and adhere to the contours thereof, as well as completely fill the void volume or excavation space.

It is another object of the present invention to efficiently utilize an entire excavation volume to increase therapeutic dosages, to optimize delivery of therapeutic agents, to administer the delivery system in small and irregularly shaped compartments, to ensure uniform, consistent therapeutic agent distribution, and to allow easy surgical implantation.

It is still another object of the present invention to incorporate biodegradable, biocompatible microspheres into the semisolid.

It is another object of the present invention to utilize an emulsification/solvent-evaporation method, spray drying methods, multiple emulsion methods as well as other methods employed in the art for producing pellets, nonpareils, microspheres, nanoparticles or other multiparticulates whereby a therapeutic agent is deposited within or upon the desired multiparticulate structures.

It is another object of the present invention to provide biodegradable, biocompatible microspheres having a therapeutic agent dispersed therein for incorporation into the semisolid delivery system so as to provide immediate, delayed, sequential, concurrent or sustained delivery of therapeutic agent(s).

Briefly described according to one embodiment of the present invention, a semisolid delivery system and combination semisolid, multiparticulate delivery system for therapeutic agents is comprised of a heterogeneous system which utilizes biocompatible, biodegradable microspheres dispersed in a semisolid, biocompatible, biodegradable semisolid delivery system for injection, placement or implantation within the body so as to facilitate local or systemic release of a therapeutic agent(s) within the body.

The semisolid delivery system is comprised of a biocompatible, biodegradable, viscous semisolid system wherein the preferred embodiment is comprised of a biodegradable hydrogel. Preferably, glyceryl monooleate, hereinafter referred to as GMO, is the intended semisolid delivery system.

The hydrogel system is produced by heating GMO above its melting point and adding a warm aqueous-based buffer, which produces a three-dimensional gelatinous composition of variable viscosity based on water content.

Under changing conditions of temperature and water content, the gel system exhibits several phases, which comprise a broad range of viscosity measures. For the purposes of this disclosure, two morphological phases are considered pertinent at room temperature and physiologic temperature and pH, although the ultimate morphological structure may be altered by active(s) or inactive(s) excipients.

The first morphological phase is a lamellar phase gel consisting of approximately 5%–15% aqueous content and approximately 95%–85% GMO content respectively.

The second morphological phase is a cubic phase gel consisting of approximately 15%–45% aqueous content and 85%–55% GMO content respectively.

According to the preferred embodiment a therapeutic agent, such as BCNU is incorporated into the gel so as to provide a system for delivery thereof.

Depending upon solubility of the chosen therapeutic agent(s) or drug compound(s), for example, whether such compound is lipophilic or hydrophilic, different methods are applied for combining the drug and GMO.

Upon incorporation of BCNU into GMO, the viscosity of the resulting gel decreases slightly depending on drug concentration, thus facilitating easier manipulation thereof when employing a modified large bore delivery apparatus.

It is recognized that alternative semisolids and methods of production exist such that the lipophilic nature of the semisolid can be altered, or in the alternative, the aqueous channels contained within the semisolid can be altered. Thus, various therapeutic agents in varying concentrations may diffuse from the semisolid at differing rates, or be released therefrom over various time/concentration profiles.

Because the semisolid delivery system is malleable, it can be delivered and manipulated in an implant site so as to conform to and adhere to all areas of the resection walls thereof, as well as to completely fill the void volume. The semisolid delivery system ensures intimate tissue contact, thorough distribution and uniform delivery throughout the resection walls of a resection pocket. Ease of delivery and manipulation of the delivery system within resection pockets is facilitated via the modified large bore semisolid delivery apparatus. The modified large bore semisolid delivery apparatus facilitates targeted and controlled placement of the delivery system.

The multiparticulate component is comprised of biodegradable, biocompatible, polymeric or non-polymeric systems utilized to produce solid structures including but not limited to nonpareils, pellets, crystals, agglomerates, microspheres, or nanoparticles.

In one embodiment, the multiparticulate component is comprised of biodegradable poly(lactic-co-glycolide) hereinafter referred to as PLGA. As H2O penetrates the PLGA polymer, the ester bonds thereof are hydrolyzed, and monomers, being water soluble, are removed from the PLGA polymer, thus facilitating release of an entrapped drug from within the PLGA polymer microsphere.

The PLGA polymer microspheres are produced via an emulsification/ solvent-evaporation method, which is extended as a non-limiting example of methods to produce these structures. The emulsification/solvent-evaporation method produces spherical multiparticulates whereby the therapeutic agent is dispersed within the system. Following agitation and removal of non-aqueous solvents by evaporation, and final processing procedures, the microspheres are ready for incorporation into the semisolid delivery system.

The present invention further serves to fill the void volume left following the removal or erosion of pathological or diseased tissues, and in so doing, reduces edema, inflammation and the unwanted loss or migration of body fluid(s).

The use of the present invention allows void volumes to be filled with a biodegradable, biocompatible semisolid system which provides an immediate, delayed, sequential, concurrent and/or sustained, local or systemic delivery of drugs and therapeutic agents. As such, it is envisioned that the delivery system can be utilized to deliver antibiotics used to treat infectious diseases including fungal abscesses and bacterial abscesses. It is further envisioned that the delivery system can be utilized to deliver experimental neuroprotective agents directly to the CNS following trauma or stroke. It is still further envisioned that one embodiment of the delivery system can be formulated and utilized for direct application to body tissues as a hemostatic agent. It is still further envisioned that the delivery system can be formulated and utilized for direct application to body tissues for topical drug delivery of agents to be used for the treatment of surgical wounds, general abrasions, lacerations and decubitus ulcers.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENT

1. Detailed Description of the Invention

A semisolid therapeutic delivery system and combination semisolid, multiparticulate, therapeutic delivery system for therapeutic agents is provided. According to the present invention, comprised of a delivery system which utilizes a semisolid, biodegadable, biocompatible delivery system or a biodegradable, biocompatible multiparticulate dispersed and suspended in a semisolid, biodegradable, biocompatible biodegradable delivery system for injection, deposition or implantation within or upon the body so as to facilitate local or systemic therapeutic effects. For purposes of this disclosure, the term "biodegradable" means material that will degrade actively or passively over time by simple chemical processes, by action of body enzymes or by other similar mechanisms in the human body. The term "biocompatible" means causing no clinically relevant tissue irritation or necrosis at local site necessitating removal of the device prior to end of therapy based on a clinical risk/benefit assessment. The terms "in the body", "void volume", "resection pocket", "excavation", "injection site", "deposition site" or "implant site" are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof.

Figure 1:
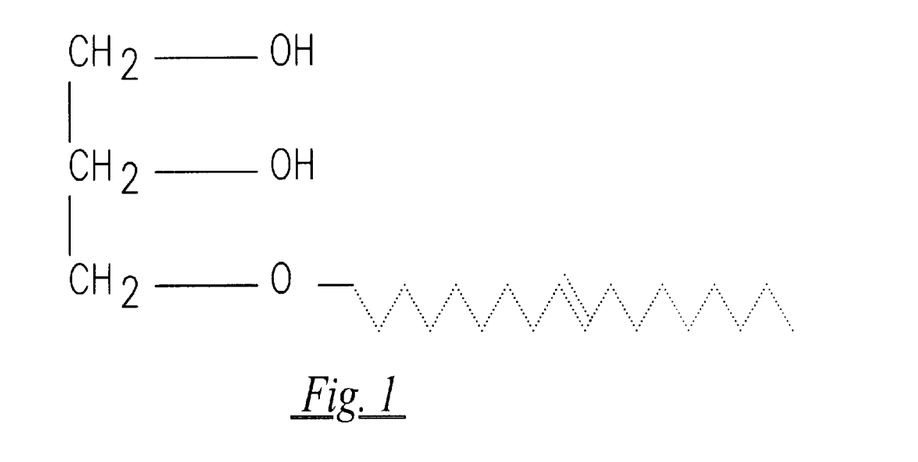
FIG. 1 illustrates the chemical formula of glyceryl monooleate.

The semisolid delivery system is comprised partially or in whole of a biocompatible, biodegradable, viscous semisolid wherein the semisolid, according to the preferred embodiment, is comprised of a hydrogel. For purposes of this disclosure, the term "hydrogel" means a substance resulting in a solid, semisolid, pseudoplastic, or plastic structure containing a necessary aqueous component to produce a gelatinous or jelly-like mass. The hydrogel incorporates and retains significant amounts of H2O, which will eventually reach an equilibrium content in the presence of an aqueous environment. Preferably, glyceryl monooleate, hereinafter referred to as GMO, is the intended semisolid delivery system or hydrogel. The chemical structure for GMO is shown in FIG. 1. It is envisioned, however, that many hydrogels, polymers, hydrocarbon compositions and fatty acid derivatives having similar physical/chemical properties with respect to viscosity/rigidity could function as a semisolid delivery system for purposes of this invention.

Figure 2:
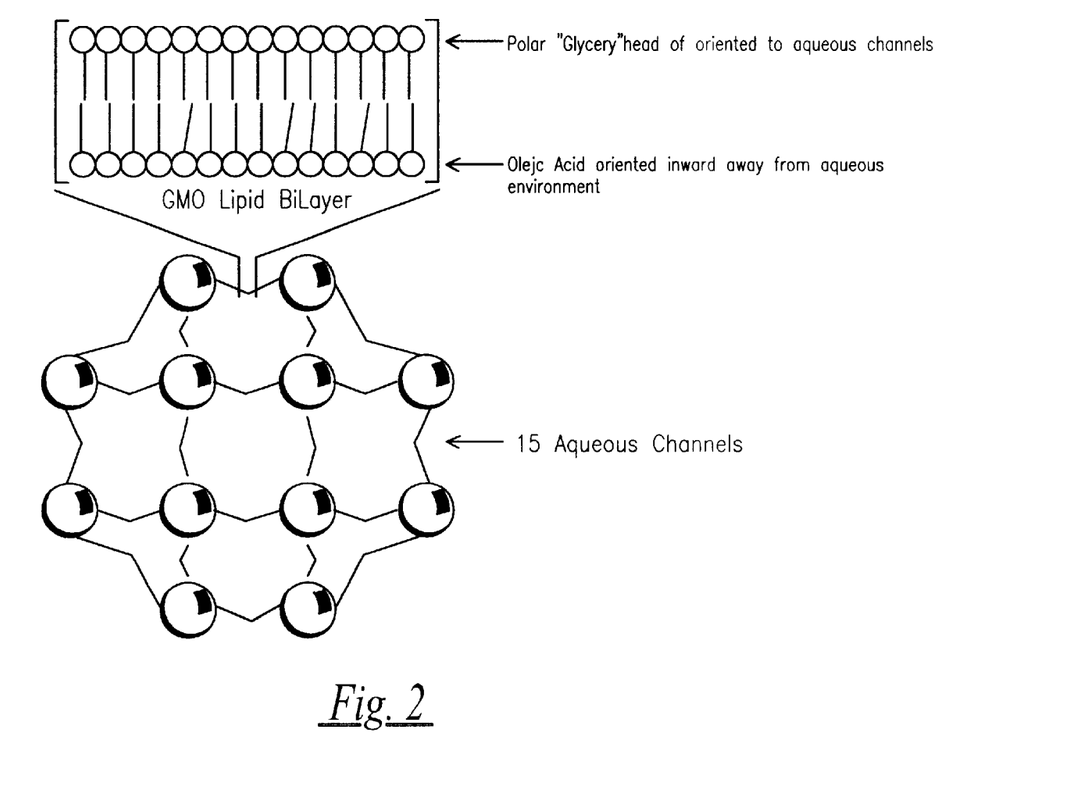
FIG. 2 shows hydrogel depicted as a three-dimensional structure having internal aqueous channels.

According to the preferred embodiment, the gel system is produced by heating GMO above its melting point (40° C.–50° C.) and adding a warm aqueous-based buffer or electrolyte solution, such as phosphate buffer or normal saline, which thus produces a three-dimensional structure, as shown in FIG. 2. The aqueous-based buffer disclosed is meant only as a suggestion and is in no way limiting. The aqueous-based buffer may be comprised of other aqueous solutions or combinations containing semi-polar solvents.

GMO provides a predominantly lipid-based hydrogel, which has the ability to incorporate lipophilic materials. For purposes of this disclosure, the term "lipophilic" means preferring or possessing an affinity for a non-polar environment compared to a polar or aqueous environment. GMO further provides internal aqueous channels 15, shown in FIG. 2, which serve to incorporate and deliver hydrophilic compounds as well. For purposes of this disclosure, the term "hydrophilic" means a material or substance having an affinity for polar substances such as water. It is recognized that at room temperature, the gel system exhibits differing phases which comprise a broad range of viscosity measures. Room temperature is defined as between 20° C. to 25° C. for purposes of the present invention. For purposes of this disclosure, two gel system phases are considered pertinent at room temperature and physiologic temperature and pH (approximately 37° C., and approximately pH 7.4).

The first phase is a lamellar phase consisting of approximately 5%–15% H2O content and approximately 95%–85% GMO content respectively. The lamellar phase is a moderately viscous fluid, which can be easily manipulated, poured and injected.

The second phase is a cubic phase consisting of approximately 15%–40% H2O content and approximately 85%–60% GMO content respectively, and has an equilibrium water content at approximately 35%–40% by weight. For purposes of this disclosure, the phrase "equilibrium water content" means maximum water content in the presence of excess water. Thus the cubic phase incorporates water at approximately 35–40% by weight. The cubic phase is highly viscous, as measured via a Brookfield viscometer. The viscosity exceeds 1.2 million centipoise (cp); wherein 1.2 million cp being the maximum measure of viscosity obtainable via the cup and bob configuration of the Brookfield viscometer.

According to the preferred embodiment a therapeutic agent, such as BCNU or carmustine is incorporated into the semisolid so as to provide a system for sustained, continuous delivery thereof. BCNU is sold under the trade name BiCNU®. The chemical name for BCNU is 1,3-bis[2-chloroethyl]-1-nitrosourea. For purposes of this disclosure, it is envisioned that other therapeutic agents, biologically-active agents, drugs, medicaments and inactives may be incorporated into the semisolid for providing a local or systemic biological, physiological, or therapeutic effect in the body at various release rates.

Incorporation of Therapeutic Agents into GMO Hydrogel

Depending upon solubility of the chosen drug compound, for example, whether such compound is lipophilic or hydrophilic, different methods are applied for combining the drug and GMO. For example, BCNU is lipophilic, thus BCNU is first combined with GMO. The BCNU-GMO combination is then melted and the GMO solubilizes the lipophilic agent (BCNU). Upon incorporation of BCNU into GMO, the viscosity of the resulting gel decreases slightly, thus facilitating easier manipulation thereof when employing a modified large bore semisolid delivery apparatus 20, shown in FIGS. 3 and 4.

In the alternative, a water-soluble drug compound is first combined with a warm aqueous-based buffer system, such as H2O, then heated, and finally combined with melted GMO so as to form a gel.

Alternative Semisolid Formulations

Figure 5:
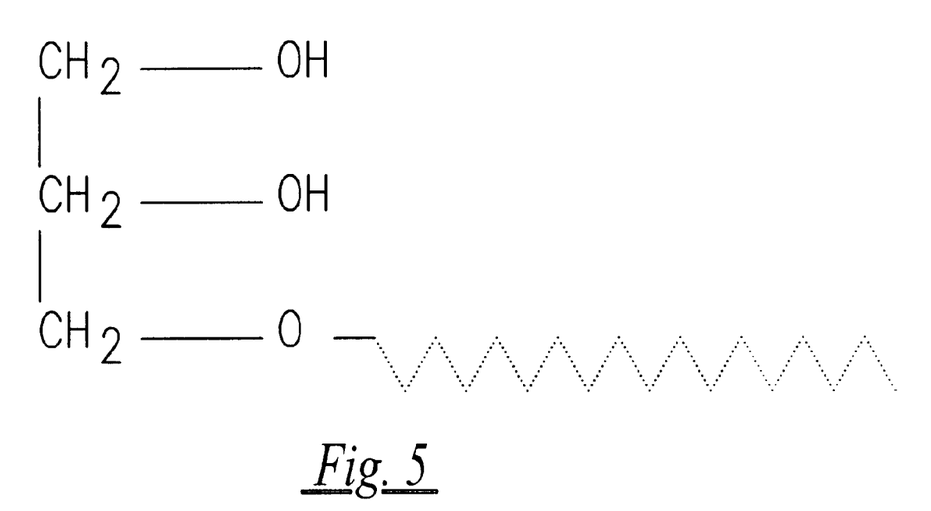
FIG. 5 illustrates the chemical formula of glyceryl monostearate.

It is recognized that alternative semisolids, modified formulations and methods of production exist such that the lipophilic nature of the semisolid can be altered, or in the alternative, the aqueous channels 15 contained within the semisolid can be altered. Thus, various therapeutic agents in varying concentrations may diffuse from the semisolid at differing rates, or be released therefrom over time via the aqueous channels 15 of the semisolid. Hydrophilic substances may be utilized to alter semisolid consistency or drug release by alteration of viscosity, fluidity, surface tension or the polarity of the aqueous component. For example, glyceryl monostearate (GMS), as shown in FIG. 5, which is structurally identical to GMO with the exception of a double bond at Carbon 9 and Carbon 10 of the fatty acid moiety rather than a single bond, does not gel upon heating and the addition of an aqueous component, as does GMO. However, because GMS is a surfactant, GMS is miscible in H2O up to approximately 20% weight/weight. For purposes of this disclosure, the term "surfactant" means surface active agent, thus being miscible in H2O in limited concentrations as well as polar substances. Upon heating and stirring, the 80% H2O/20% GMS combination produces a spreadable paste having a consistency resembling hand lotion. The paste is then combined with melted GMO so as to form the cubic phase gel, possessing a high viscosity as stated heretofore.

Alternatively, hydrolyzed gelatin, trade name Gelfoam®, is utilized for altering the aqueous component. Approximately 6.25% to 12.50% concentration of Gelfoam® by weight placed in approximately 93.75% to 87.50% concentration of H2O respectively by weight or other aqueous based buffer. Upon heating and stirring, the H2O/Gelfoam® combination produces a thick gelatinous substance. The resulting substance is combined with GMO, whereby a product so formed swells and forms a highly viscous, translucent gel being less malleable in comparison to neat GMO gel alone.

In addition, polyethylene glycols (PEG's) may be utilized for altering the aqueous component to aid in drug solubilization. Approximately 0.5% to 40% concentration of PEG's (depending on PEG molecular weight) by weight placed in approximately 99.5% to 60% concentration of H2O respectively by weight or other aqueous based buffer. Upon heating and stirring, the H2O/PEG combination produces a viscous liquid to a semisolid substance. The resulting substance is combined with GMO, whereby a product so formed swells and forms a highly viscous gel.

The drug, such as BCNU, releases from the semisolid through diffusion, conceivably in a biphasic manner. A first phase involves, for example, a lipophilic drug contained within the lipophilic membrane diffuses therefrom into the aqueous channel 15. The second phase involves diffusion of the drug from the aqueous channel 15 into the external environment. Being lipophilic, BCNU orients itself inside the GMO gel within its proposed lipid bi-layer structure. Thus, incorporating greater than approximately 7.5% BCNU by weight into GMO causes a loss of the integrity of the three-dimensional structure whereby the gel system no longer maintains the semisolid cubic phase, and reverts to the viscous lamellar phase liquid.

Application of Semisolid Delivery System

It is possible to incorporate approximately 7.5% BCNU by weight into GMO gel at physiologic temperature without disruption of the normal three-dimensional structure. In addition, an average glioma tumor measures approximately 3 centimeters in diameter and equates to approximately 14 cubic centimeters in volume. As a result, approximately 11.5 to 12.0 grams of GMO gel may be implanted into the resection pocket. This equates to a possible drug dosage of approximately 900 milligrams with maximal drug. As stated earlier, the clinically recommended dose of BCNU delivered by Gliadel® Wafers to date is approximately 65 milligrams. Thus, this system allows the ability of significantly increased flexibility with drug dosages.

Figure 3:
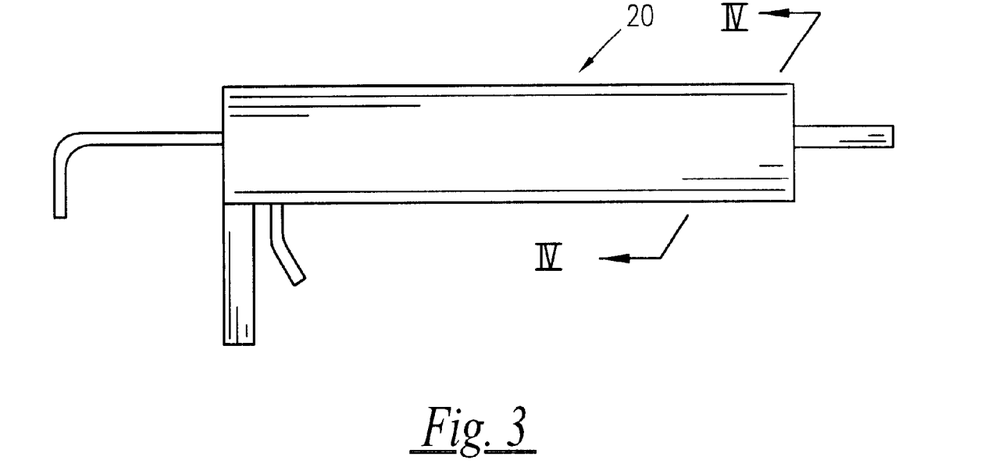
FIG. 3 is a perspective view of the modified large bore semisolid delivery apparatus according to the preferred embodiment of the present invention.
Figure 4:
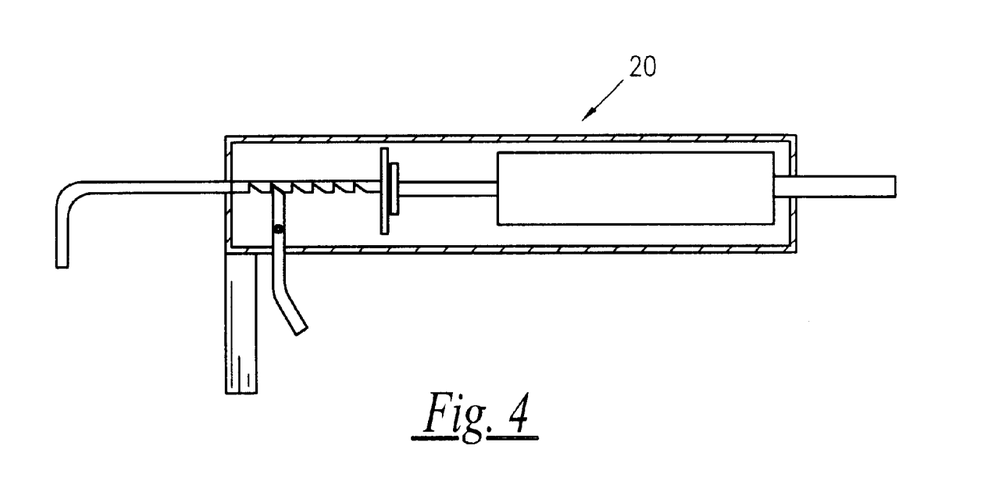
FIG. 4 is a cross-sectional view of the modified large bore semisolid delivery apparatus taken along line IV—IV of FIG. 3.

Because the delivery system is malleable, it can be delivered and manipulated in an implant site so as to adhere and conform to contours of resection walls or other voids in the body as well as completely fill all voids existing. The delivery system ensures drug distribution and uniform drug delivery throughout the resection walls of a resection pocket. Ease of delivery and manipulation of the delivery system within resection pockets is facilitated via the modified large bore semisolid delivery apparatus 20. The modified large bore semisolid delivery apparatus facilitates targeted and controlled delivery of the delivery system.

Biocompatible, Biodegradable Multiparticulate

The multiparticulate component is comprised of biocompatible, biodegradable, polymeric or non-polymeric systems utilized to produce solid structures including but not limited to nonpareils, pellets, crystals, agglomerates, microspheres, or nanoparticles.

According to the preferred embodiment, the multiparticulate component is comprised of poly(lactic-co-glycolide) hereinafter referred to as PLGA's. PLGA's are biodegradable polymer materials used for controlled and extended therapeutic agent delivery within the body. Such delivery systems offer enhanced therapeutic efficacy and reduced overall toxicity as compared to frequent periodic, systemic dosing. It is envisioned that PLGA's systems consisting of differing molar ratios of the monomeric subunits will facilitate greater flexibility in engineering precise release profiles for accommodating targeted therapeutic agent delivery through alterations in the rate of polymer degradation. The PLGA composition, according to the preferred embodiment of the present invention, is sufficiently pure so as to be biocompatible and remains biocompatible upon biodegradation. Preferably, the PLGA polymer is designed and configured into microspheres having a therapeutic agent or drug entrapped therein, whereby the therapeutic agent is subsequently released therefrom by a method to be described in greater detail below.

The preferred embodiment of the present invention further utilizes the multiparticulate component being comprised of poly d,l(lactic-co-caprolactone). This system is a biodegradable polymer material used for controlled and extended therapeutic agent delivery within the body with a similar drug release mechanism to that of the PLGA polymers.

It is envisioned that the multiparticulate microspheres can also be produced using biodegradable and/or biocompatible non-polymeric materials such as GMS.

It is further envisioned that the aforementioned embodiments and envisioned embodiments will be further modified by methods used to encapsulate or coat the multiparticulate components using polymers of the same composition with the same or different drug substances, different polymers with the same or different drug substances, or with multiple layering processes containing no drug, the same drug, a different drug, or multiple drug substances. This will allow the production of a multi-layered (encapsulated) multiparticulate system with a wide range of drug release profiles for single or multiple drug agents simultaneously. In addition, it is envisioned that coating materials which control the rate of physical drug diffusion from the multiparticulate may be utilized alone or in concert with the aforementioned preferred embodiments and envisioned embodiments.

Drug Release Mechanism

The PLGA polymer contains ester bonds, which are labile to hydrolysis. For purposes of this disclosure, the term "labile" means subject to increased degradation. When H2O penetrates the PLGA polymer, the ester bonds thereof are hydrolyzed, and monomers, being water soluble, are removed from the PLGA polymer, thus facilitating the physical release of the entrapped drug over time. It is both recognized and envisioned that other classes of synthetic biodegradable, biocompatible polymers may be used for controlled and extended therapeutic agent delivery within the body, including polyanhydrides, poly(phosphates), polydioxanone, cellulosics and acrylics which are extended as non-limiting examples. It is further envisioned that non-polymeric materials may be utilized for controlled and extended therapeutic agent delivery within the body, including but not limited to sterols, sucrose fatty acid esters, fatty acids, and cholesteryl esters, which are extended as non-limiting examples.

Production Method for PLGA Polymer Microsphere for Incorporation into GMO Gel According to the preferred embodiment, the PLGA polymer microspheres are produced via an emulsification/solvent-evaporation method. Such method comprises the following steps:

(a) dissolve both therapeutic agent, preferably BCNU, and PLGA polymer in a suitable solvent, preferably methylene chloride. The solubility of a polymeric material in a particular solvent will vary according to factors such as polymeric material's hydrophilicity, lipophilicity, and crystallinity;

(b) transfer BCNU, PLGA polymer, and methylene chloride to an aqueous buffer system in a ratio of approximately 1.5:1 to 2:1 (aqueous component: polymer solution) having an emulsifying agent, preferably polyvinyl alcohol, which thus form small droplets or spheres, wherein formation of spheres being the emulsification step; and (c) agitate spheres for 15–30 minutes at room temperature;

(d) increase the temperature to approximately 40–45° C. and continue agitation for approximately 90–115 minutes;

(e) remove spheres from heat and agitation, collect spheres by filtration and wash with distilled water;

(f) collect spheres in a suitable container, flash freeze to −70° C. and dry in a lyophilizer at −40° C. for 48 hours.

Employing the emulsification/solvent-evaporation method produces a solution whereby therapeutic agent is homogeneously dispersed throughout the polymer system. Once formed, collected, washed and dried the microspheres are ready for incorporation into the semisolid.

The spheres can also be formed by other common techniques such as spray drying methods as is commonly known in the art. This results in spheres of differing morphology, density and porosity.

In Vitro Release of BCNU from GMO Hydrogels

Utilization of 200 milligram easily reproducible, molded columnar devices dimensioned to approximately 6 mm diameter, 6 mm height provided in vitro sustained release of BCNU over a 24-hour period into an aqueous phosphate buffer. Comparable release periods as to GMO gel alone were obtained when utilizing both GMS/GMO gel and Gelfoam®/GMO gel combinations.

Utilization of a 1.4 gram molded columnar GMO gel device dimensioned to approximately 9 mm diameter, 12 mm height provided a sustained release of BCNU over a 48-hour period in both a 2.5% and 5.0% concentration of GMO gel by weight.

Implantation of a delivery system into the body where the aqueous environment becomes significantly altered, drug release is determined by the solubility of the drug, diffusion and convection in extracellular fluid. Given the significantly different conditions of the in vitro experiments with respect to implantation volume and aqueous release medium, it is anticipated that the semisolid alone will offer significantly sustained delivery of therapeutic agents ranging from days to weeks in duration. It is further anticipated that implanting the present invention into brain tissue in significant volumes using GMO gel in combination with drug incorporated PLGA polymer microspheres will provide sustained drug delivery for a plurality of months.

The present invention not only provides a delivery system for sustained local or systemic delivery of drugs and therapeutic agents, but has other significant applications as well.

The present invention serves to fill the void volume left tissue resection, and in so doing, reduces the possibility of tissue and fluid shifts. It is envisioned that the delivery system can be utilized to treat infectious diseases of the central nervous system including fungal abscesses and bacterial abscesses. Here, the present invention could be injected into an abscess pocket following drainage so as to facilitate a very high, localized concentration of antibiotics. As an additional utility to this application, the semisolid system has demonstrated a resistance to microbial growth within or upon the semisolid mass upon exposure to microbial challenges.

The present invention further may be formulated as a useful hemostatic agent. When the semisolid delivery system is formulated so as to have a low aqueous or semi-polar solvent content and is exposed to a high aqueous content environment, (i.e. blood, lymph etc.), a zone which is in direct contact with the aqueous environment hydrates and rapidly forms a solid cubic phase. To date, this hemostatic effect has been observed in animal studies. This is of significant importance when under conditions where rapid hemostasis is necessary. Such is the case when performing neurosurgery and brain tissue is injured. Upon injury, brain tissue bleeds and oozes diffusely. However, introducing the present invention directly to bleeding vessels actuates acute swelling of the gel and subsequent transition thereof to the terminal cubic phase, which thus serves to tamponade the vessels. The more quickly a surgeon performs and completes brain surgery directly correlates with recovery time and ability of a patient to completely recover post operatively.

It is further envisioned that the present invention may be utilized for delivery of experimental agents at the time of post-operative evacuation of a hematoma resulting from stroke. The chronic damage of a stroke is caused by the breakdown products of a clot. Thus insult associated with the breakdown products and their removal from the brain is required so as to improve the neural function and recovery of patients with stroke. There are several classes of compounds such as capsase inhibitors, which may play a role in reducing tissue damage associated with the cascade of the breakdown products of clots within the brain. However, these classes of compounds have been generally of limited utility because of very poor penetration into the central nervous system. Thus, it is envisioned that the incorporation and administration of a neuroprotective agent with the present invention and implanting or injecting such at the time of clot removal would serve to alleviate neural damage associated with a residual clot.

It is further envisioned that the present invention may be utilized for delivery of therapeutic agents to pathological conditions of the skin or superficial structures of the body such as decubitus ulcers (bed sores) and surgical sound infections. The system can be formulated to delivery useful agents such as antibiotics to treat or control infection as well as to fill voids and form a physical barrier to the external environment.

2. Operation of the Preferred Embodiment

To use the present invention, a semisolid system, which acts as a vehicle for systemic and local delivery of therapeutic agents, is comprised of lipophilic, hydrophilic or amphophilic, solid or semisolid, heated above its melting point and thereafter followed by inclusion of a warm aqueous component so as to produce a gelatinous composition of variable viscosity based on water content. The therapeutic agent(s) is incorporated and dispersed into the melted lipophilic component or the aqueous buffer component prior to mixing and formation of the semisolid system. The gelatinous composition is placed within a modified large bore semisolid delivery apparatus for subsequent placement, or deposition . Being malleable, the gel system is easily delivered and manipulated via the modified large bore semisolid delivery apparatus in an implant site, where it adheres and conforms to contours of resection walls or other voids in the body as well as completely filling all voids existing. Alternatively, a multiparticulate component, comprised of a biocompatible polymeric or non-polymeric system, is utilized for producing microspheres having a therapeutic agent entrapped therein. Following final processing methods, the microspheres are incorporated into the semisolid system and subsequently placed within the modified large bore semisolid delivery apparatus so as to be easily delivered therefrom into an implant sight or comparable space, whereby the therapeutic agent is subsequently released therefrom by (a) drug release mechanism(s). This delivery system is envisioned to offer enhanced therapeutic efficacy and reduced overall toxicity as compared to frequent periodic, systemic dosing.

The use of the present invention allows for a void space resulting from a surgical procedure, pathological condition or other such body tissue to be filled or deposited with a biocompatible semisolid or biocompatible combination semisolid, multiparticulate, which provides a delivery system for immediate or sustained local or systemic delivery of drugs and therapeutic agents.

Therefore, the foregoing description is included to illustrate the operation of the preferred embodiment and is not meant to limit the scope of the invention. As one can envision, an individual skilled in the relevant art, in conjunction with the present teachings, would be capable of incorporating many minor modifications that are anticipated within this disclosure. Therefore, the scope of the invention is to be broadly limited only by the following claims.

What is claimed is:

1. A semisolid therapeutic delivery system and combination semisolid, multiparticulate therapeutic delivery system for therapeutic agents comprising:
   a biodegradable, biocompatible semisolid delivery system, said semisolid delivery system designed for injection, deposition, or implantation within or upon a body so as to provide local therapeutic effects, facilitate local or systemic release of therapeutic agents(s) in or on said body;
   a biodegradable, biocompatible combination semisolid, multiparticulate delivery system for injection, deposition, or implantation within or upon said body to provide local therapeutic effects, facilitate local or systemic release of therapeutic agent(s) in or on said body, wherein said biodegradable, biocompatible combination semisolid, multiparticulate delivery system is defined as a biocompatible, biodegradable material having biodegradable, biocompatible multiparticulate(s) dispersed within a biocompatible, biodegradable viscous semisolid.

2. The semisolid therapeutic delivery system and combination semisolid, multiparticulate therapeutic delivery system for therapeutic agents of claim 1, wherein said body is defined as all internal and external tissues including but not limited to spaces formed via injections, surgical incisions, tumor or tissue removal, abscess formation, tissue injuries and other comparable assessment, treatment, or physiologic response to disease, injury or pathology.

3. The semisolid therapeutic delivery system and combination semisolid, multiparticulate therapeutic delivery system for therapeutic agents of claim 1, wherein said semisolid delivery system is selected from the group consisting of biocompatible, biodegradable, semisolids having a lipophilic nature, wherein said semisolids are comprised of a hydrogel, and wherein said hydrogel is a substance formed of a solid structure or a semisolid structure exhibiting a pseudoplastic or a plastic behavior containing a necessary aqueous component for producing a gelatinous or jelly-like mass.

4. The semisolid therapeutic delivery system and combination semisolid, multiparticulate therapeutic delivery system for therapeutic agents of claim 3, wherein said hydrogel incorporates and retains significant amounts of H2O so as to eventually reach an equilibrium content in presence of said aqueous component.

5. The semisolid therapeutic delivery system and combination semisolid, multiparticulate therapeutic delivery system for therapeutic agents of claim 4, wherein said aqueous component is a buffer of electrolyte solution selected from the group consisting of phosphate buffers, H2O, and normal saline.

6. The semisolid therapeutic delivery system and combination semisolid, multiparticulate therapeutic delivery system for therapeutic agents of claim 4, wherein said hydrogel has the ability to incorporate clinically significant concentrations of lipophilic materials.

7. The semisolid therapeutic delivery system and combination semisolid, multiparticulate therapeutic delivery system for therapeutic agents of claim 6, wherein said hydrogel is glyceryl monooleate.

8. The semisolid therapeutic delivery system and combination semisolid, multiparticulate therapeutic delivery system for therapeutic agents of claim 7, wherein said GMO hydrogel is utilized to solubilize and stabilize compounds at concentrations necessary to provide therapeutic benefits.

9. The semisolid therapeutic delivery system and combination semisolid, multiparticulate therapeutic delivery system for therapeutic agents of claim 3, wherein said hydrogel, under specific levels of hydration, develops a three-dimensional structure composed of internal aqueous channels which serve to incorporate and deliver hydrophilic compounds when present and lipophilic structural walls which serve to incorporate and deliver lipophilic compounds when present, wherein said hydrogel being produced by heating said semisolid precursor above a melting point of said semisolid precursor and adding a warm said aqueous component.

10. The semisolid therapeutic delivery system and combination semisolid, multiparticulate therapeutic delivery system for therapeutic agents of claim 9, wherein said hydrogel exhibits differing gel system phases of differing viscosities based aqueous content at room temperature, wherein said room temperature being defined as between 20° C. to 25° C., and wherein said differing gel system phases comprise a lamellar phase and a cubic phase, wherein said lamellar phase and said cubic phase being the pertinent gel phases at room temperature and physiologic temperature and pH, wherein said physiologic temperature is approximately 37° C. and said pH is approximately pH 7.4.

11. The semisolid therapeutic delivery system and combination semisolid, multiparticulate therapeutic delivery system for therapeutic agents of claim 10, wherein said lamellar phase consists of approximately 5% to 15% H2O content and approximately between 95% and 85% said glyceryl monooleate content respectively in the absence of drugs, medicaments or excipients that may alter the specific phase state.

12. The semisolid therapeutic delivery system and combination semisolid, multiparticulate therapeutic delivery system for therapeutic agents of claim 11, wherein said lamellar phase is defined as a moderately viscous fluid being easily manipulated, poured and injected.

13. The semisolid therapeutic delivery system and combination semisolid, multiparticulate therapeutic delivery system for therapeutic agents of claim 10, wherein said cubic phase consists of approximately 15% to 45% H2O content and approximately between 85% and 55% said glyceryl monooleate respectively, and wherein said cubic phase has an equilibrium water content at approximately 35% to 40% by weight in the absence of drugs, medicaments or excipients that may alter the specific phase state.

14. The semisolid therapeutic delivery system and combination semisolid, multiparticulate therapeutic delivery system for therapeutic agents of claim 13, wherein said cubic phase is defined as being highly viscous, and wherein said cubic phase has a viscosity measure which exceeds 1.2 million centipoise.

15. The semisolid therapeutic delivery system and combination semisolid, multiparticulate therapeutic delivery system for therapeutic agents of claim 3, wherein said hydrogel is incorporated with a therapeutic agent so as to provide a system for immediate, sustained, or continuous delivery of said therapeutic agent.

16. The semisolid therapeutic delivery system and combination semisolid, multiparticulate therapeutic delivery system for therapeutic agents of claim 15, wherein said therapeutic agent is a lipophilic compound.

17. The semisolid therapeutic delivery system and combination semisolid, multiparticulate therapeutic delivery system for therapeutic agents of claim 16, wherein said lipophilic compound is 1,3-bis[2-chloroethyl]-1-nitrosourea.

18. A method of incorporating a lipophilic therapeutic agent(s) into a semisolid, comprising the steps of:
    (1) combining said lipophilic therapeutic agent with said semisolid, thus producing a therapeutic agent/semisolid product; and
    (2) melting said product whereby said semisolid solubilizes said lipophilic therapeutic agent so as to form a resulting semisolid having a viscosity which is slightly decreased with respect to said semisolid alone, thus facilitating easier manipulation of said resulting semisolid.

19. The method of claim 18, wherein said lipophilic therapeutic agent is said 1,3-bis[2-chloroethyl]-1-nitrosourea, and said semisolid is said glyceryl monooleate.

20. A method of incorporating a hydrophilic therapeutic agent(s) into a semisolid, comprising the steps of:
    (1) melting said semisolid;
    (2) combining said hydrophilic therapeutic agent with a warm aqueous component;
    (3) heating hydrophilic therapeutic agent/aqueous component combination; and
    (4) combining said hydrophilic therapeutic agent/aqueous component combination with melted semisolid so as to form a malleable semisolid.

21. The method of claim 20, wherein said aqueous component is buffered to physiological conditions, and said semisolid is said glyceryl monooleate.

22. The semisolid therapeutic delivery system and combination semisolid, multiparticulate therapeutic delivery system for therapeutic agents of claim 3, wherein said lipophilic nature of said semisolids can be altered by utilizing alternative semisolids, modified formulations, and alternative methods of production so as to allow various therapeutic agents in varying concentrations to diffuse from said semisolids at differing rates or be released from said semisolids over time via internal aqueous channels of said semisolids.

23. The semisolid therapeutic delivery system and combination semisolid, multiparticulate therapeutic delivery system for therapeutic agents of claim 22, wherein said internal aqueous channels of said semisolids are altered by said modified formulations and said methods of production so as to allow said various therapeutic agents in varying concentrations to diffuse from said semisolids at differing rates or be released from said semisolids over time via said internal aqueous channels of said semisolids.

24. A method of producing an alternative semisolid comprising the steps of:
    (1) melting said glyceryl monooleate;
    (2) combining a hydrophilic surfactant with H2O;
    (3) heating and stirring hydrophilic surfactant/H2O combination so as to produce a spreadable paste; and
    (4) combining said spreadable paste with melted glyceryl monooleate so as to form an alternative cubic phase gel possessing high viscosity.

25. The method of claim 24, wherein said hydrophilic surfactant is glyceryl monostearate, and wherein said glyceryl monostearate is a surfactant agent miscible in H2O up to approximately 20%, thereby producing an 80% H2O/20% glyceryl monostearate combination.

26. The method of claim 24, wherein said hydrophilic surfactant is polyethylene glycol, and wherein said polyethylene glycol is a surfactant agent miscible in $H_2O$ from 0.5% to 40% based on molecular weight, thereby producing a 99.5% to 60% $H_2O$/polyethylene glycol combination.

27. The semisolid therapeutic delivery system and combination semisolid, multiparticulate therapeutic delivery system for therapeutic agents of claim 5, wherein said aqueous buffer having a surface tension or polarity being alterable when used in conjunction with hydrophilic substances which thus serves to alter a consistency of said semisolids or to alter drug release rates from said semisolids.

28. A method of altering an aqueous buffer comprising the steps of:
    (1) placing approximately 6.25% to 12.50% concentration of hydrolyzed gelatin by weight in approximately 93.75% to 87.50% concentration of said aqueous buffer, respectively, thus producing a hydrolyzed gelatin/aqueous buffer combination;
    (2) heating and stirring said combination which produces a thick gelatinous substance; and
    (3) combining said thick gelatinous substance with glyceryl monooleate so as to form a product which swells and forms a highly viscous, translucent gel being less malleable with regard to neat glyceryl monooleate alone.

29. The semisolid therapeutic delivery system and combination semisolid, multiparticulate therapeutic delivery system for therapeutic agents of claim 15, wherein said therapeutic agent(s) release(s) from said hydrogel in a biphasic process, wherein said biphasic process consists of a first phase and a second phase.

30. The semisolid therapeutic delivery system and combination semisolid, multiparticulate therapeutic delivery system for therapeutic agents of claim 29, wherein said first phase is defined as where a lipophilic therapeutic agent contained within the lipophilic membrane of said hydrogel diffuses from said lipophilic membrane into said aqueous channel of said hydrogel, and wherein said second phase is defined as diffusion of said lipophilic therapeutic agent from said aqueous channel into an external environment.

31. The semisolid therapeutic delivery system and combination semisolid, multiparticulate therapeutic delivery system for therapeutic agents of claim 30, wherein said lipophilic therapeutic agent is 1,3-bis[2-chloroethyl]-1-nitrosourea, and wherein said hydrogel is glyceryl monooleate.

32. The semisolid therapeutic delivery system and combination semisolid, multiparticulate therapeutic delivery system for therapeutic agents of claim 31, wherein said 1,3-bis[2-chloroethyl]-1-nitrosourea is oriented within a lipid bi-layer structure of said glyceryl monooleate, and upon incorporation of greater than approximately 7.5% of said 1,3-bis[2-chloroethyl]-1-nitrosourea by weight into said glyceryl monooleate causes a loss of integrity of said three-dimensional structure of said glyceryl monooleate, whereby said semisolid delivery system no longer maintains said cubic phase and reverts to said lamellar phase.

33. The semisolid therapeutic delivery system and combination semisolid, multiparticulate therapeutic delivery system for therapeutic agents of claim 3, wherein said semisolid delivery system is malleable and is easily delivered and manipulated in an implant site where said semisolid delivery system adheres to and conforms to contours of resection walls of resection pockets or other voids in said body as well as fill all existing voids, thereby ensuring therapeutic distribution and uniform therapeutic delivery throughout said resection walls of said resection pockets, and thus further providing significantly increased flexibility with therapeutic dosages.

34. The semisolid therapeutic delivery system and combination semisolid, multiparticulate therapeutic delivery system for therapeutic agents of claim 1, wherein said biocompatible multiparticulate is comprised of polymeric or non-polymeric systems utilized to produce solid structures with targeted release rates and reduced overall toxicity as compared to frequent periodic, systemic dosing.

35. The semisolid therapeutic delivery system and combination semisolid, multiparticulate therapeutic delivery system for therapeutic agents of claim 34, wherein said solid structures are selected from the group consisting of nonpareils, pellets, crystals, agglomerates, microspheres, and nanoparticles.

36. The semisolid therapeutic delivery system and combination semisolid, multiparticulate therapeutic delivery system for therapeutic agents of claim 34, wherein said biocompatible multiparticulate is poly(lactic-co-glycolide), and wherein said poly(lactic-co-glycolide) is a biodegradable polymer material used for controlled and extended therapeutic agent delivery within said body, and wherein said poly(lactic-co-glycolide) having a composition remaining biocompatible upon biodegradation.

37. The semisolid therapeutic delivery system and combination semisolid, multiparticulate therapeutic delivery system for therapeutic agents of claim 36, wherein said poly(lactic-co-glycolide) consists of differing molar ratios of monomeric subunits for facilitating greater flexibility in engineering precise release profiles for accommodating targeted said therapeutic agent delivery through alterations in rate of polymer degradation.

38. The semisolid therapeutic delivery system and combination semisolid, multiparticulate therapeutic delivery system for therapeutic agents of claim 34, wherein said biocompatible multiparticulate is poly d,l(lactic-co-caprolactone), and wherein said poly d,l(lactic-co-caprolactone) is a biodegradable polymer material used for controlled and extended therapeutic agent delivery within said body.

39. The semisolid therapeutic delivery system and combination semisolid, multiparticulate therapeutic delivery system for therapeutic agents of claim 34, wherein said biocompatible polymeric multiparticulate is encapsulated or coated with a desired, suitable polymer of a same composition with a same or different therapeutic substances so as to allow for production of an encapsulated multiparticulate system having a wide range of therapeutic release profiles for single or multiple therapeutic agents simultaneously.

40. The semisolid therapeutic delivery system and combination semisolid, multiparticulate therapeutic delivery system for therapeutic agents of claim 34, wherein said biocompatible, polymeric, multiparticulate is encapsulated or coated with a desired, suitable polymer of a different composition with a same or different therapeutic substances, so as to allow for production of an encapsulated multiparticulate system having a wide range of therapeutic release profiles for single or multiple therapeutic agents simultaneously.

41. The semisolid therapeutic delivery system and combination semisolid, multiparticulate therapeutic delivery system for therapeutic agents of claim 34, wherein said biocompatible multiparticulate is encapsulated or coated with a single or multiple encapsulating processes containing either no therapeutic agent, the same therapeutic agent, or a plurality of therapeutic agents, so as to allow for production of an encapsulated multiparticulate system having a wide range of therapeutic release profiles for single or multiple therapeutic agents simultaneously.

42. The semisolid therapeutic delivery system and combination semisolid, multiparticulate therapeutic delivery system for therapeutic agents of claim 36, wherein said poly(lactic-co-glycolide) is designed and configured into said microspheres via an emulsification/solvent-evaporation method, wherein said therapeutic agent or a drug is entrapped in said microspheres, whereby said therapeutic agent or said drug is subsequently released from said microspheres via a drug release mechanism.

43. The semisolid therapeutic delivery system and combination semisolid, multiparticulate therapeutic delivery system for therapeutic agents of claim 42, wherein said poly(lactic-co-glycolide) contains ester bonds which are labile to hydrolysis, whereupon subsequent penetration by H2O of said poly(lactic-co-glycolide) actuates hydrolyzation of said ester bonds, and monomers being water soluble, are removed from said poly(lactic-co-glycolide), thus facilitating physical release of said therapeutic agent or said drug over time.

44. The semisolid therapeutic delivery system and combination semisolid, multiparticulate therapeutic delivery system for therapeutic agents of claim 34, wherein said polymeric or non-polymeric systems are selected from the group consisting of polyanhydrides, poly(phosphates), polydioxanone, cellulosics, acrylics, sterols, sucrose, fatty acid esters, fatty acids, and cholesteryl esters.

45. A method of producing poly(lactic-co-glycolide) polymer microsphere for incorporation into semisolid comprising the steps of:
 (1) dissolving suitably desired therapeutic agent and said poly(lactic-co-glycolide) polymer in a suitable solvent;
 (2) transferring said suitably desired therapeutic agent, said poly(lactic-co-glycolide) polymer, and a suitable solvent to an aqueous buffer having an emulsifying agent in a ratio of approximately 1.5:1 to 2.0:1 (aqueous buffer: polymer solution), which thus forms small droplets or microspheres;
 (3) agitating said microspheres for 15–30 minutes at room temperature;
 (4) increasing the temperature to approximately 40° C. to 45° C. and continuing agitation for approximately 90–115 minutes;
 (5) removing said microspheres from heat and agitation, collecting said microspheres by filtration, and washing said microspheres with distilled water;
 (6) collecting said microspheres in a suitable container, flash freezing said microspheres to −70° C. and drying in a lyophilizer at −40° C. for 48 hours; and
 (7) incorporating said microspheres into said semisolid.

46. The method of claim 45, wherein said suitably desired therapeutic agent is said 1,3-bis[2-chloroethyl]-1-nitrosourea, said suitable solvent is methylene chloride, and said emulsifying agent is polyvinyl alcohol.

47. The semisolid therapeutic delivery system and combination semisolid, multiparticulate therapeutic delivery system for therapeutic agents of claim 42, wherein said emulsification/solvent-evaporation method produces a solution whereby said therapeutic agent is homogeneously dispersed throughout said poly(lactic-co-glycolide) polymer.

48. The semisolid therapeutic delivery system and combination semisolid, multiparticulate therapeutic delivery system for therapeutic agents of claim 1, wherein said semisolid delivery system serves to fill a void volume left by tissue resection, thus reducing a possibility of tissue and fluid shifts.

49. The semisolid therapeutic delivery system and combination semisolid, multiparticulate therapeutic delivery system for therapeutic agents of claim 1, wherein said semisolid delivery system and said combination semisolid multiparticulate delivery system can be injected into an abscess pocket, stemming from infectious diseases of central nervous system such as fungal abscesses and bacterial abscesses, following drainage so as to facilitate a very, high, localized concentration of antibiotics.

50. The semisolid therapeutic delivery system and combination semisolid, multiparticulate therapeutic delivery system for therapeutic agents of claim 1, wherein said semisolid delivery system resists microbial growth within or upon said semisolid delivery system upon exposure to microbial challenges.

51. The semisolid therapeutic delivery system and combination semisolid, multiparticulate therapeutic delivery system for therapeutic agents of claim 1, wherein said semisolid delivery system is formulated with a low aqueous or semi-polar solvent content so as to provide a formulation which facilitates hemostasis.

52. The semisolid therapeutic delivery system and combination semisolid, multiparticulate therapeutic delivery system for therapeutic agents of claim 51, wherein said formulation being exposed to or in direct contact with a high aqueous content environment, such as blood or lymph, creates a zone of contact between said formulation and said high aqueous content environment, whereby said zone hydrates and forms a solid cubic phase.

53. The semisolid therapeutic delivery system and combination semisolid, multiparticulate therapeutic delivery system for therapeutic agents of claim 1, wherein said semisolid delivery system and said combination semisolid multiparticulate therapeutic delivery system are designed and configured to deliver said therapeutic agents to pathological conditions of skin or superficial structures of said body such as decubitus ulcers and surgical sound infections.

54. The semisolid therapeutic delivery system and combination semisolid, multiparticulate therapeutic delivery system for therapeutic agents of claim 1, wherein said semisolid delivery system and said combination semisolid multiparticulate therapeutic delivery system may be incorporated with a neuroprotective agent for implantation or injection in said body at a time of post-operative evacuation of a hematoma resulting from stroke so as to alleviate neural damage associated with a residual clot.

55. The semisolid therapeutic delivery system and combination semisolid, multiparticulate therapeutic delivery system for therapeutic agents of claim 1, wherein said semisolid and said combination semisolid multiparticulate delivery system are incorporated with members selected from the group consisting of biologically-active agents, drugs, medicaments, inactives, other therapeutic agents, and chemically modified equivalents and combinations thereof for providing a local or systemic biological, physiological, or therapeutic effect in said body.

* * * * *